United States Patent [19]
Dutton

[11] Patent Number: 4,999,929
[45] Date of Patent: Mar. 19, 1991

[54] AUTOMATIC HAND-SANITIZING SYSTEM
[75] Inventor: Virgil R. Dutton, Chandler, Ariz.
[73] Assignee: Core Medical Corporation, Mesa, Ariz.
[21] Appl. No.: 359,845
[22] Filed: May 31, 1989
[51] Int. Cl.⁵ .............................................. F26B 19/00
[52] U.S. Cl. ........................................ 34/90; 34/202
[58] Field of Search ...................... 128/200.11, 200.12, 128/200.13, 200.14, 200.20, 200.21; 34/90, 202; 422/298, 305, 306, 292

[56] References Cited
U.S. PATENT DOCUMENTS
2,311,899  2/1943  Marlowe ............................. 34/90 X Primary Examiner—Henry A. Bennet
Attorney, Agent, or Firm—Woodard, Emhardt, Naughton, Moriarty & McNett

[57] ABSTRACT

A wall-mounted housing encloses a blower, an antiseptic solution holder, an atomizer pump, and a timer-switch assembly. A front-mounted actuator bar initiates a timer which starts the blower and pump. The atomizer delivers antiseptic solution into the blower discharge for delivery of a vapor mist through the nozzle to the hands of the user for a pre-determined period of time established by the timer. Then the atomizer is shut down by the timer and the blower continues to operate for another predetermined period to dry the hands.

7 Claims, No Drawings

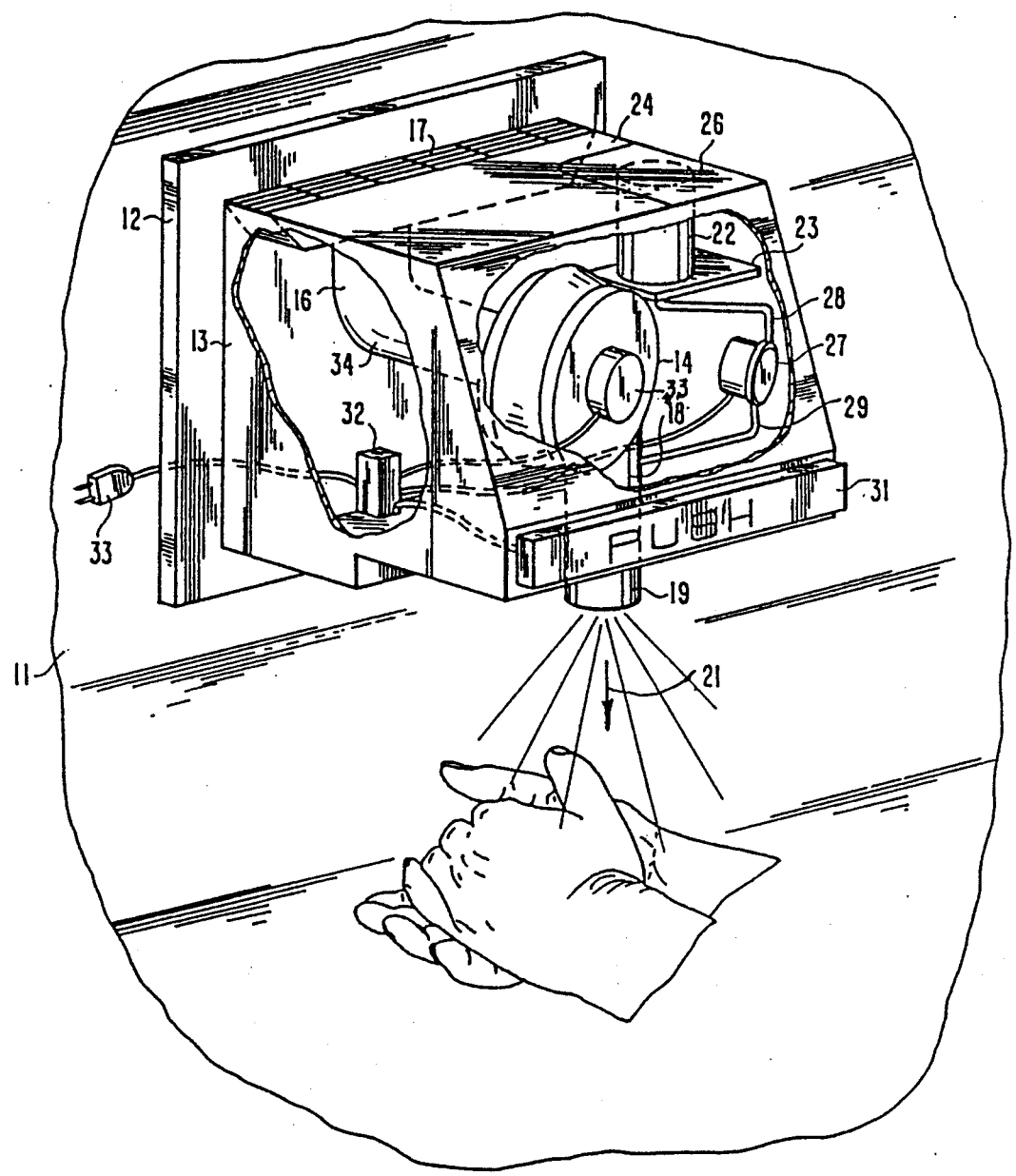

AUTOMATIC HAND-SANITIZING SYSTEM

BACKGROUND OF THE INVENTION

This invention relates generally to sanitation equipment, and more particularly to apparatus for cleaning hands without the use of a liquid wash.

In medical care environments, particularly in coronary care units (CCU) and intensive care units (ICU), the maintenance of very sanitary conditions is extremely important, and cross-contamination between patients must be avoided. Therefore, conscientious attendants may feel compelled to wash hands as they move from one patient to the next. But often there is no visible evidence of any foreign matter on the hands. Even so, the usual sanitizing procedure is washing with hot water and antiseptic soap solution or the like, rinsing and drying. This procedure requires some time and, if too frequent or rigorous, may result in skin irritation. But the prior art known to me provides no suitable alternative. Wall-mounted hand dryer blowers may be helpful to avoid aggravation during the drying step, but their function is only to dry hands by a blast of air.

SUMMARY OF THE INVENTION

Described briefly, according to a typical embodiment of my invention, there is apparatus which includes a nozzle from which a vapor mist and drying air can be discharged. There is a container to hold antiseptic solution. An atomizer pump takes solution from the container, breaks it into a fine spray, and introduces it into the upstream side of the nozzle. An air blower is provided to take room air and discharge it through the nozzle. A sequence initiator is coupled to the atomizer and blower and, when pushed, will start a timer coupled to the atomizer and blower to start operation of both of them. The atomizer will introduce antiseptic solution into the blower discharge for delivery of a vapor mist through the nozzle for a pre-determined period of time established by the timer. The atomizer will then be shut down by the timer and the blower will continue to operate for another predetermined period.

In the use of the apparatus, the person places one hand under the nozzle, pushes the initiator bar and places the other hand under the nozzle. A vapor mist of antiseptic solution is delivered from the nozzle for five to ten seconds. Then the vapor mist automatically shuts off and dry air continues to flow from the nozzle to dry the hands. The hands may be wrung together in whatever manner desired by the user during the discharge of the vapor mist, and during the continued operation of the blower for the drying period.

BRIEF DESCRIPTION OF THE DRAWING

The single figure of drawing illustrates a wall-mounted apparatus according to a typical embodiment of the present invention, with portions of the housing broken away to show interior details.

DESCRIPTION OF THE PREFERRED EMBODIMENT

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawing in detail, a vertical wall 11 of a building has the apparatus of the present invention secured to it by a mounting plate 12 fastened to the wall, and the housing 13 fastened to the mounting plate. A blower 14 mounted in the housing has an air intake duct 16 receiving room air through the intake grille 17. The blower has a discharge duct 18 directed through the bottom of the housing from which the discharge nozzle 19 projects. The duct 18 and nozzle 19 are sealed together so that the blower discharge all exits through the nozzle 19 in the general direction of the arrow 21. For convenience of use, the housing should be mounted on the wall 11 at a height such that the bottom of the discharge nozzle would be located at an elevation between 34 and 54 inches above the floor.

A bottle 22 containing antiseptic solution is mounted on the shelf 23 inside and near the top 24 of the housing. An access door 26 is mounted at the top of the housing to permit addition of solution to the bottle, when desired.

An atomizer pump 27 is mounted in the housing and has an intake line 28 from the bottom of the bottle and a discharge line 29 to the discharge duct 18 of the blower. A timer-switch assembly 32 has an electrical power input from the supply cord 33, or it may be directly connected to the building wiring (a more typical installation). The timer-switch assembly 32 has outputs coupled to the blower motor 34 and to the atomizer pump 27. A push-actuated bar 31 at the lower front of the housing, is coupled to the timer-switch assembly 32 and, when pushed, starts the timer which closes two power switches, one to the atomizer pump and one to the blower motor. Under control of the timer, the one switch will open in about five to seven seconds after bar 31 is pushed, to terminate action of the atomizer pump. Under control of the timer, the other switch will open in about ten seconds after the bar is pushed, to thereupon terminate operation of the blower.

Details of the assembly 32 and the mechanical coupling to the bar 31 and electrical couplings to the blower and atomizer are not described herein, because devices for the individual functions of these components are readily available and well known in the art.

OPERATION

In the operation of the present invention, the attendant simply pushes the bar 31 with one hand while holding the other under the nozzle. This action initiates the timer-switch 32 which energizes the blower motor 33 and the atomizer pump 27. As indicated above, the timer is set up so that the blower motor will operate approximately 10 seconds from the initiation of the action by pushing the bar 31. It is also set up so that the atomizer will operate only 5 to 7 seconds and then be shut off by the timer switch.

After pushing bar 31, the user will put their other hand under the nozzle and the nozzle will discharge a vapor mist of the antiseptic solution which is sufficient to wet the hands and be rubbed about, but not sufficient to create a dripping problem. When the misting is stopped by the timer, the blower continues to operate and dries the hands. The user can then proceed with sterilized hands, to attend to the next patient.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A hand sanitizing apparatus comprising:
   a housing;
   outlet means on said housing for discharge of fluid from said housing;
   a blower coupled to said outlet means for blowing air out of said outlet means;
   a container containing antiseptic fluid;
   means coupled to said container and said outlet means for taking antiseptic fluid from said container, and delivering antiseptic fluid to said outlet means; and
   timing and switching means coupled to said blower and to said means for delivering, to maintain simultaneous operation of said blower and said means for delivering for a first discrete period and then terminate operation of said means for delivering while maintaining operation of said blower for an additional period.

2. The apparatus of claim 1 and wherein:
   said blower and said means for delivering are arranged so that a fog of antiseptic is delivered from said outlet means.

3. A hand sanitizing apparatus comprising:
   a housing having top and bottom surfaces;
   a fluid discharge outlet;
   a blower coupled to said discharge outlet for blowing air out of said outlet;
   a container containing antiseptic fluid; and
   an atomizer coupled to said container and to said outlet for taking antiseptic fluid from said container, and delivering antiseptic fluid in atomized liquid form to said discharge outlet.

4. The apparatus of claim 3 and further comprising:
   timing and switching means coupled to said blower and atomizer and operable to maintain simultaneous operation of said blower and atomizer for a first discrete period and then terminate operation of said atomizer while maintaining operation of said blower for an additional period.

5. The apparatus of claim 4 and further comprising:
   a push-operated initiator exposed at the exterior of said housing and coupled to said timing and switching means to start operation of said blower and atomizer.

6. The apparatus of claim 4 and wherein:
   said timing and switching means are arranged such that said first period has a duration of about five to seven seconds, and said additional period has a duration of about three to five seconds.

7. The apparatus of claim 6 and wherein the outlet is a nozzle in the bottom surface of the housing to cause the blower discharge to produce a blast of air downward from the nozzle, the apparatus further comprising:
   an upstanding mounting wall,
   said housing being mounted to the wall in a location facilitating the placement of user hands under the nozzle for use of the apparatus.

* * * * *